(12) United States Patent
Kishino et al.

(10) Patent No.: US 6,733,693 B1
(45) Date of Patent: May 11, 2004

(54) ACRYLONITRILE SOLUTIONS OF MALEIMIDES, METHOD FOR PREPARATION THEREOF, AND ACRYLONITRILE BASED COPOLYMERS OBTAINED BY USE OF THE SOLUTIONS

(75) Inventors: Kazuo Kishino, Hyogo (JP); Kinichi Nakayama, Hyogo (JP); Fumioki Shimoyama, Hyogo (JP); Yuichi Kita, Hyogo (JP)

(73) Assignee: Nippon Shokubai Co., Ltd., Osaka-fu (JP)

( * ) Notice: Subject to any disclaimer, the term of this patent is extended or adjusted under 35 U.S.C. 154(b) by 0 days.

(21) Appl. No.: 09/473,415

(22) Filed: Dec. 29, 1999

Related U.S. Application Data

(62) Division of application No. 08/703,709, filed on Aug. 27, 1996, now Pat. No. 5,993,687.

(30) Foreign Application Priority Data

Aug. 29, 1995 (JP) ............................................. 7-220072
May 23, 1996 (JP) ............................................. 8-128334
Jun. 4, 1996 (JP) ............................................. 8-141256
Jul. 16, 1996 (JP) ............................................. 8-185779

(51) Int. Cl.$^7$ .................... C09K 15/35; C09K 15/24; C09K 3/00
(52) U.S. Cl. .............................. 252/400.2; 252/182.18; 252/400.23; 252/400.24; 252/404
(58) Field of Search ..................... 252/182.18

(56) References Cited

U.S. PATENT DOCUMENTS

| | | | | |
|---|---|---|---|---|
| 5,045,233 A | * | 9/1991 | Kita et al. | 252/399 |
| 5,149,827 A | * | 9/1992 | Kita et al. | 548/548 |
| 5,928,558 A | * | 7/1999 | Cunkle et al. | 252/182.18 |

FOREIGN PATENT DOCUMENTS

| | | | | |
|---|---|---|---|---|
| EP | 0323244 | * | 7/1989 | |
| EP | 0437342 | | 7/1991 | |
| JP | 03012057 B2 | * | 2/1991 | ....... C07D/207/448 |
| JP | 06-128223 | * | 5/1994 | |
| JP | 0892208 | | 4/1996 | |
| JP | 08092208 A | * | 4/1996 | ....... C07D/207/448 |

OTHER PUBLICATIONS

JP06–128223 (Ueda, et al.) 1994–05, [machine translation received from PAJ on Feb. 24, 2003].*
Derwent ACC–NO 1993–021435 "Prepn. of maleimide acrylonitrile soln. having good storage stability" JP04–346973A, Dec. 2, 1992.*
USPTO obtained translation of JP4–346973 (Dec. 2, 1992) Masayoshi Furuya.*
DERWENT machine–assisted translation of JP8–92208A (Apr. 9, 1994) Kazuo Kishino.*
USPTO obtained translation of JP 03–012057B2 (Feb. 19, 1991) Toho et al.*

* cited by examiner

Primary Examiner—Matthew A. Thexton
(74) Attorney, Agent, or Firm—Mathews, Collins, Shepherd & McKay, P.A.

(57) ABSTRACT

An acrylonitrile solution of maleimide manifesting transparency, precluding coloration and opacification during the course of handling, and excelling in stability, a method for the preparation of the acrylonitrile solution, and an acrylonitrile based copolymer obtained by using the acrylonitrile solution are provided. The acrylonitrile solution of maleimide is such that, when it is subjected to a forced coloration test, the differences $\Delta L$, $\Delta a$, $\Delta b$ values (invariably as absolute values) each between L, a, and b values before and after the test are respectively not more than 5, not more than 5, and not more than 10. The acrylonitrile solution of maleimide is prepared by lowering the water content in the acrylonitrile solution to a level of not more than 0.1% by weight, or causing the acrylonitrile solution to permit coexistence therein of a polymerization inhibitor and lowering the water content in the acrylonitrile solution to a level of not more than 0.3% by weight.

10 Claims, No Drawings

ACRYLONITRILE SOLUTIONS OF MALEIMIDES, METHOD FOR PREPARATION THEREOF, AND ACRYLONITRILE BASED COPOLYMERS OBTAINED BY USE OF THE SOLUTIONS

This application is a divisional of U.S. Ser. No. 08/703,709 filed Aug. 27, 1996, issued as U.S. Pat. No. 5,993,687, the disclosure of which is incorporated herein by reference.

BACKGROUND OF THE INVENTION

1. Field of the Invention

The present invention relates to acrylonitrile solutions of maleimides, a method for the preparation thereof, and acrylonitrile based copolymers obtained by the use of the acrylonitrile solutions.

The maleimides represented by N-phenyl maleimide and the like are used as a heat resistance enhancer for such acrylonitrile based copolymers as acrylonitrile-butadiene-styrene (ABS) resin, acrylonitrile-acrylic rubber-styrene (AAS) resin, acrylonitrile-styrene (AS) resin, and acrylonitrile-chlorinated polyethylene-styrene (ACS) resin.

2. Description of the Prior Art

The maleimides which are in a solid state at room temperature have been heretofore handled generally in such forms as powder, flakes, and tablets. The maleimides in these solid forms, however, undergo gradual comminution and yield minute particles copiously during the course of transportation and consequently give rise to numerous problems such as deterioration of the work environment. For the solution of these problems, a method for enabling the maleimides to be handled securely in the form of acrylonitrile solutions obtained in advance by dissolving the maleimides together with a polymerization inhibition in acrylonitrile (JP-B-03-12,057) has been proposed. Since this method which permits the maleimides to be handled in the form of acrylonitrile solutions is excellent in having solved the problems mentioned above, it has been finding growing acceptance for industrial applications.

Since the acrylonitrile as the solvent for the acrylonitrile solutions of maleimides constitutes itself the source of the acrylonitrile conpnent of the acrylonitrile based copolymers, the acrylonitrile solutions of maleimides, after being handled as for transportation, are used in their unmodified form for the production of the acrylonitrile based copolymers mentioned above.

The maleimides are yellow and the acrylonitrile solutions obtained by dissolving the maleimides in acrylonitrile are yellow and transparent. So long as the acrylonitrile solutions of maleimides are as yellow and transparent as they were when they were fresh from the production line, the acrylonitrile based copolymers as finished products using the solutions pose no particular problem concerning the color characteristics. In other words, the acrylonitrile based copolymers as the finished products cannot induce such coloration as tends to impair their marketability.

On no occasion, however, the acrylonitrile solutions of maleimides which are fresh from the production line are used immediately for the production of acrylonitrile based copolymers. Generally, the acrylonitrile solutions of maleimides after their production are transported by tank lorries and the like, stored in tanks and the like, or conveyed by the pipeline including pipe, valves, and nozzles (such as, for example, the polymer-feeding line from the storage tank for the acrylonitrile solutions of maleimides) before they are used for the production of acrylonitrile based copolymers. In the present invention, the transportation as by tank lorries, the storage as in tanks, and the conveyance as by the pipeline including pipe, valves, and nozzles (such as, for example, the polymer-feeding line from the storage tank for the acrylonitrile solutions of maleimides) will be referred to collectively as "handling."

After the acrylonitrile solutions of maleimides have been handled over a specific period, they possibly change color from the inherent yellow color to a brown color, for example, gain in the degree of yellowness (namely, darken the yellow color), or occasionally opacify In this invention, these phenomena will be referred to collectively as "discoloration."

The acrylonitrile based copolymers obtained as finished products by using the acrylonitrile solutions of maleimides which have been discolored as described above are colored and have markedly impaired marketability. For the purpose of improving these finished products in marketability, the standards or demands imposed on the color of the acrylonitrile solutions of maleimides have been decisively gaining in exactitude in recent years. In the circumstances, such acrylonitrile solutions of maleimides as are appropriately used for the production of acrylonitrile based copolymers which sparingly incur discoloration due to aging during the course of handling, consequently preclude coloration, and excel in the color characteristics are strongly demanded.

Hereinafter, the acrylonitrile solutions of maleimides will be occasionally referred to simply as "acrylonitrile solutions."

An object of this invention, therefore, is to provide such acrylonitrile solutions of maleimides as are appropriately used for the production of acrylonitrile based copolymers which preclude coloration and excel in the color characteristics.

Another object of this invention is to provide a method for the production of the acrylonitrile solutions of maleimides mentioned above.

Yet another object of this invention is to provide acrylonitrile based copolymers of excellent color characteristics and high marketability which are obtained by using the acrylonitrile solutions of maleimides mentioned above.

SUMMARY OF THE INVENTION

The objects mentioned above are accomplished by the following aspects (1) to (9) of the present invention.

(1) An acrylonitrile solution of maleimide, characterized by the fact that, in a forced coloration test, the values, $\Delta L$, $\Delta a$, and $\Delta b$, to be calculated in accordance with the following formulas:

$$\Delta L = |L1 - L2| \text{(Absolute value)}$$

$$\Delta a = |a1 - a1| \text{(Absolute value)}$$

$$\Delta b = |b1 - b2| \text{(Absolute value)}$$

wherein L1, a1, and b1 are respectively the values of L, a, and b of the acrylonitrile solution before undergoing the forced coloration test and L2, a2, and b2 are respectively for the values or L, a, and b of the acrylonitrile solution after undergoing the forced coloration test, are respectively not more than 5, not more than 5, and not more than 10.

(2) An acrylonitrile solution of N-phenylmaleimide having azobenzene and N,N-diphenyl hydrazine at a total content of not more than 500 ppm.

(3) A method for the preparation of an acrylonitrile solution set forth in (1) or (2) mentioned above, characterized in that the acrylonitrile solution has a water content of not more than 0.1% by weight.

(4) A method for the preparation of an acrylonitrile solution set forth in (1) or (2) mentioned above, characterized in that the acrylonitrile solution allows the presence therein of at least one member selected from the group consisting of alkyl-substituted hydroxybenzenes and hindered phenols and at least one member selected from the group consisting of phosphorous esters, phosphoric esters, phosphine, and phosphoric acid amides.

(5) A method for the preparation of an acrylonitrile solution set forth in (1) or (2) mentioned above, characterized in that the acrylonitrile solution has a water content adjusted to a level of not more than 0.3% by weight and allows the presence therein of at least one member selected from the group consisting of alkyl-substituted hydroxybenzenes and hindered phenols, phosphorous esters, phosphoric esters, phosphine, and phosphoric acid amides.

(6) A method for the storage of an acrylonitrile solution of maleimide set forth in (1) or (2) mentioned above, characterized in that the molecular oxygen concentration of the gaseous phase portion of the acrylonitrile solution is adjusted to a level in the range of 0.01 to 10% by volume preparatorily to storing the solution as held in contact with a metal.

(7) A method for the preparation of an acrylonitrile solution of maleimide set forth in (1) or (2) mentioned above, comprising the steps of causing a molten maleimide obtained by purifying crude maleimide to allow the presence therein of a primary antioxidant and a secondary antioxidant and subsequently dissolving the solidified maleimide in acrylonitrile.

(8) A method for the preparation of an acrylonitrile solution of maleimide set forth (1) or (2) mentioned above, characterized in that the molten maleimide obtained by purifying crude maleimide is dissolved in acrylonitrile in the presence of a primary antioxidant and a second antioxidant.

(9) An acrylonitrile based copolymer obtained by the use of an acrylonitrile solution set forth in (1) or (2) mentioned above.

It is well known that as one of the methods for quantitatively rating the difference between two colors, the so-called Hunter's L, a, b method has been proposed by Richard S. Hunter [Richard S. Hunter, The Measurement of Appearance, 2nd Ed., John Wiley & Sons, (1987)]. An instrument generally called a colorimeter which permits direct reading of the L, a, b values according to the Hunter's L, a, b method mentioned above is marketed and is readily available. We have decided to indicate the degree of discoloration of an acrylonitrile solution of maleimide by using the differences in L, a, and b values determined with a colorimeter designed on the basis of the Hunter's L, a, b method mentioned above. To be specific, we have established a method of forced coloration test for reproducing the discoloration by aging which occurs when the acrylonitrile solution is actually handled on a commercial scale and rated the degree of discoloration of the acrylonitrile solution in terms of the differences in the L, a, and b values before and after the test. We have consequently found that an acrylonitrile solution giving not more than 5, not more than 5, and not more than 10 respectively as the values of $\Delta L$, $\Delta a$, and $\Delta b$ calculated in accordance with the following formulas:

$\Delta L=|L1-L2|$(Absolute value)

$\Delta a=|a1-a1|$(Absolute value)

$\Delta b=|b1-b2|$(Absolute value)

wherein L1, a1, and b1 are respectively the values of L, a, and b before the test mentioned above and L2, a2, and b2 are respectively for the values of L, a, and b after the test, when copolymerized, produces an acrylonitrile based copolymer, more specifically an acrylonitrile-maleimide-containing copolymer, precluding discoloration, excelling in color characteristics, and enjoying high marketability. The acrylonitrile solution of maleimide of this invention incurs no or markedly diminished discoloration by aging during the course of handling thereof.

We made a study in search of the cause for discoloration of the acrylonitrile solutions of maleimides, particularly N-phenyl maleimide. We have consequently demonstrated that the substances responsible for the discoloration are azobenzene (occasionally referred to briefly as "AZB" hereinafter) and N,N'-diphenyl hydrazine (occasionally referred to briefly as "DPH" hereinafter). We have further found that acrylonitrile based copolymers, specifically acrylonitrile-N-phenyl maleimide-containing copolymers, obtained with an acrylonitrile solution of N-phenyl maleimide whose total content of AZB and DPH is not more than 500 ppm (based on the weight of the acrylonitrile solution) preclude discoloration and enjoy extremely high marketability.

We seek to explain the formation of AZB and DPH in the acrylonitrile solution of N-phenyl maleimide as follows, though not intent on restricting the present invention by a theoretical discussion. When the acrylonitrile solution of N-phenyl maleimide is stored in a tank made of carbon steel or stainless steel, since the standard industry grade acrylonitrile contains water in a small amount such as, for example, in the approximate range of 0.5 to 1% by weight, this water acts and causes the N-phenyl maleimide to undergo partial hydrolysis and first produce aniline and then this aniline, when activated, leads to the formation of AZB and DPH via the aniline radical.

We have found that the acrylonitrile solution of maleimide having not more than 5, not more than 5, and not more than 10 respectively as the values of $\Delta L$, $\Delta a$, and $\Delta b$ and the acrylonitrile solution of N-phenyl maleimide containing AZB and DPH in a total amount of not more than 500 ppm can be prepared by lowering the water content thereof to not more than 0.1 by weight or by adding such an antioxidant as an alkyl-substituted hydroxybenzene and hindered phenol thereto.

Incidentally, the maleimide to be used for the preparation of the acrylonitrile solution of maleimide is generally in the form of flakes of maleimide which are obtained by purifying crude maleimide by distillation in the presence of a polymerization inhibitor thereby obtaining molten maleimide, temporarily storing the molten maleimide in an intermediate tank, and then cooling and solidifying the molten maleimide by the treatment with a flaker, for example. Generally, the flakes of maleimide are stored as placed in a packing container such as, for example, a paper bag, a container bag, or an alumina container. At times, this storage extends over a period of several months. The flakes of maleimide are inevitably exposed to the ambience of air before they are dissolved in acrylonitrile. Specifically, the maleimide is exposed to the ambience of air during the step of storing the molten maleimide in the intermediate tank, the step of cooling and solidifying the molten maleimide into flakes, and the step of storing the flakes of maleimide.

We have been ascertained by their study that the maleimide, when exposed to the ambience of air before it is dissolved in acrylonitrile, is disposed to form readily a peroxide as a source of radical and produce actually the peroxide in a very minute amount and that this peroxide directly passes into the acrylonitrile solution of maleimide, participates in the formation of substances responsible for coloration, and induces unfavorable results such as the discoloration of the acrylonitrile solution of maleimide.

The idea of carrying out the steps mentioned above in the ambience of nitrogen may be conceived for the solution of this problem. This method, however, is incapable of effectively preventing the molten maleimide from being polymerized and is unrealistic from the viewpoint of economy, for example.

We have further continued their study to find that the formation of the peroxide in the maleimide and the discoloration by aging of the acrylonitrile solution of maleimide can be very effectively prevented by quickly adding the combination of such antioxidants as generally defined as a primary antioxidant and a secondary antioxidant to the maleimide which is yet to be solidified, specifically to the maleimide which has been purified by distillation and is still in the molten state.

PREFERRED EMBODIMENT OF THE INVENTION

The present invention provides an acrylonitrile solution of maleimide, characterized by the fact that, in a forced coloration test performed by immersing a sample of the acrylonitrile solution of maleimide in a Pyrex test tube, with a size of 18 mm in inside diameter and 180 mm height, then introducing into the solution a preparatorily polished test piece made of SUS 304 and measuring 50 mm in length, 10 mm in width, and 2 mm in thickness, adjusting the molecular oxygen concentration of the gaseous phase of the test tube to a level in the range of 3 to 10% by volume (providing that the molecular oxygen concentration is obtained of the gas mixture excluding maleimide and acrylonitrile on the basis of volume), placing the test tube in an oil bath set at 70° C. and allowing it to stand therein for three days (72 hours), subsequently extracting the test piece from the test tube, and subjecting the acrylonitrile solution to the determination of the values, L , a, and b, the values, $\Delta L$, $\Delta a$, and $\Delta b$, to be calculated in accordance with the following formulas:

$\Delta L = |L1 - L2|$ (Absolute value), $\Delta a = |a1 - a1|$ (Absolute value), $\Delta b = |b1 - b2|$ (Absolute value)

wherein L1, a1, and b1 are respectively the values of L, a, and b of the acrylonitrile solution before undergoing the forced coloration test mentioned above and L2, a2, and b2 are respectively for the values of L, a, and b of the acrylonitrile solution after undergoing the forced coloration test, are respectively not more than 5, not more than 5, and not more than 10.

Incidentally, the L, a, and b values of the acrylonitrile solution of maleimide are determined by the following method.

Method for Determination of L, a, and b Values

By the use of a calorimeter produced by Nippon Denshoku Kogyo K. K. and marketed under product code of "Σ-80," a sample of the acrylonitrile solution of maleimide is adjusted to a concentration of 30% by weight and subsequently measured for the L, a, and b values by the transmission mode. A commercially available acrylonitrile (guaranteed reagent) is used as a control and the cell used for the test has a thickness of 10 mm.

The maleimides which are used in this invention include N-methyl maleimide, N-ethyl maleimide, N-hexyl maleimide, N-octyl maleimide, N-dodecyl maleimide, N-benzyl maleimide, N-cyclohexyl maleimide, N-phenyl maleimide, N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, and N-tribromophenyl maleimide, for example. Among other maleimides cited above, N-phenyl maleimide proves particularly advantageous for the use contemplated herein.

This invention does not discriminate the maleimide to be used therein on account of the method to be adopted for the production thereof. The maleimides obtained by varying methods can be used herein. For example, the maleimides obtained by the method which comprises subjecting a maleamic acid, the precursor of a maleimide, to dehydrocyclization with an acid anhydride such as acetic anhydride, the method which comprises heating a maleamic acid together with an acid catalyst under a reduced pressure thereby effecting dehydrocyclization of the maleamic acid, the method which comprises heating a maleamic acid in an organic solvent while expelling from the reaction system the water formed by the resultant dehydrocyclization in the form of an azeotropic mixture with the organic solvent, and the method which comprises preparing as an organic solvent a mixed solvent consisting of an inert organic solvent such as benzene and a non-protonic polar organic solvent such as N',N-dimethyl formamide and heating a maleamic acid in the mixed solvent thereby effecting dehydrocyclization of the maleamic acid can be used. The maleimides produced by some, if not all, of these methods contain a residual acid component. This invention tolerates the presence in the maleimide of up to about 5% by weight of such an acid component. It nevertheless prefers the maleimide to be used after being refined until the content of the acid component thereof falls below 0.3% by weight.

Advantageously, the acrylonitrile solution of maleimide of the present invention is such that the values of $\Delta L$, $\Delta a$, and $\Delta b$ are respectively not more than 5, not more than 5, and not more than 10, preferably not more than 2, not more than 2, and not more than 4, more preferably not more than 1, not more than 1, and not more than 2, and particularly preferably not more than 0.5, not more than 0.5, and not more than 1. The dissolution of maleimide in acrylonitrile can be implemented by any arbitrary method such as, for example, throwing the maleimide into acrylonitrile. Properly, the solution of maleimide is carried out at a temperature not exceeding the boiling point of acrylonitrile (78.5° C.). Since acrylonitrile has a high vapor pressure, it is generally advantageous to carry out the dissolution process at a temperature in the range of 30 to 70° C. Generally, the temperature at which the acrylonitrile solution is handled is in the range of 20 to 70° C.

The materials of which the facilities (including pipelines) for handling the acrylonitrile solution are made are not limited particularly. The surfaces of the facilities exposed to the acrylonitrile solution may be passivated by glass lining, ceramic coating, etc. For handling the acrylonitrile solution on a commercial scale, it is economically favorable to use facilities which are made of such a general-purpose industrial material as carbon steel or stainless steel.

The concentration of maleimide in the acrylonitrile solution is not particularly limited. It can be suitably selected in consideration of such factors as the temperature of handling, the form of handling (such as transportation or storage), the kind of the acrylonitrile based copolymer to be produced with the acrylonitrile solution, the method of this production, and the production conditions. In some cases, the concentration of maleimide is preferably high as when the acrylonitrile solution is used for the production of an acrylonitrile based copolymer having a high maleimide content, for example. Generally, the concentration of maleimide is in the range of 40 to 90% by weight.

Preferably, the acrylonitrile solution of maleimide of this invention is such that the values of L, a, and b to be determined after the preparation of the solution are in the ranges, L=90 to 100, a=−10 to −30, and b=30 to 50. In the acrylonitrile solutions of maleimide according to this invention, those whose values of L, a, and b determined after the preparation thereof fall within the ranges, L=90 to 100, a=−10 to −30, and b=30 to 50 and whose values of ΔL, Δa, and Δb are respectively not more than 5, not more than 5, and not more than 10, particularly preferably not more than 1, not more than 1, and not more than 2.

The acrylonitrile solution of maleimide of this invention can be efficiently produced by the methods which will be described specifically hereinbelow. These methods are adopted advantageously when the acrylonitrile solution of maleimide is handled with facilities which are made of such a general-purpose industrial material as carbon steel or stainless steel.

Method A comprises adjusting the water content in the acrylonitrile solution or maleimide to not more than 0.1% by weight (refer to Example 9).

The acrylonitrile solution of this invention cannot be prepared when the water content exceeds 0.1% by weight (refer to Controls 1 to 3). For the purpose of lowering the water content in the acrylonitrile solution to a level of not more than 0.1% by weight, since the maleimide contains substantially no water, it suffices to lower the water content in the acrylonitrile used as the solvent to a level not more than 0.1% by weight. The water content in the acrylonitrile can be adjusted by any of the known methods such as, for example, precision distillation, physical adsorption by the use of silica gel or molecular sieve, or dehydration by the use of anhydrous sodium sulfate or anhydrous magnesium sulfate. Appropriately, the water content in the acrylonitrile solution is as low as possible. The lower limit of the water content is suitably decided in consideration of the cost for minimizing the water content besides the extent of discoloration by aging which the acrylonitrile solution is expected to tolerate.

It is particularly advantageous to lower the water content in the acrylonitrile solution to a level of not more than 0.05% by weight. When the water content is thus lowered, the acrylonitrile solution to be prepared is such that the values of ΔL, Δa, and Δb thereof are respectively not more than 1, not more than 1, and not more than 2.

Method B resides in enabling the acrylonitrile solution to coexist with an antioxidant effective in precluding the generation of peroxide. As the antioxidant, at least one member selected from the group consisting of alkyl-substituted hydroxy benzenes and hindered phenols or at least one member selected from the group consisting of phosphorous esters, phosphoric esters, phosphine, and phosphoric acid amides can be used by itself. It is, however, effective to use at least one member selected from the group consisting of alkyl-substituted hydroxy benzenes and hindered phenols in combination with at least one member selected from the group consisting of phosphorous esters, phosphoric esters, phosphine, and phosphoric acid amides. Further, in Method B, the acrylonitrile solution of this invention can be prepared with high efficiency by lowering the water content in the acrylonitrile to be used. In this case, it suffices to lower the water content in the acrylonitrile solution to a level of not more than 0.3% by weight.

Thus, preferred embodiments of Method B are as follows.

(a) The water content in the acrylonitrile solution is lowered to a level of not more than 0.3% by weight and at least one member selected from the group consisting of alkyl-substituted hydroxy benzenes and hindered phenols or at least one member selected from the group consisting of phosphorous esters, phosphoric esters, phosphine, and phosphoric acid amides is caused to exist in the acrylonitrile solution (refer to Example 12).

(b) The water content in the acrylonitrile solution is lowered to a level of not more than 0.3% by weight and at least one member selected from the group consisting of alkyl-substituted hydroxy benzenes and hindered phenols and at least one member selected from the group consisting of phosphorous esters, phosphoric esters, phosphine, and phosphoric acid amides is caused to exist in the acrylonitrile solution (refer to Example 11).

In the embodiments (a) and (b) mentioned above, the discoloration by aging of the acrylonitrile solution can be diminished to a still lower level by lowering the water content in the acrylonitrile solution to a level of not more than 0.2% by weight, preferably to a level of not more than 0.1% by weight. Particularly when the water content in the acrylonitrile solution is lowered to a level of not more than 0.05% by weight, the acrylonitrile solution whose values of ΔL, Δa, and Δb are respectively not more than 1, not more than 1, and not more than 2 can be prepared.

As typical examples of the alkyl-substituted hydroxy benzene mentioned above, 2,4-dimethyl-6-tert-butylphenol, 4-tert-butyl catechol, 2,5-di-tert-butyl hydroquinone, 2-tert-butyl hydroquinone, and 4,4'-thio-bis(6-tert-butyl-m-cresol) may be cited.

As typical examples of the hindered phenol mentioned above, 2,4-bis(n-octylthio)-6-(4-hydroxy-3,5-di-tert-butyl anilino)-1,3,5-triazine, 2,2'-thiobis-(4-methyl-6-tert-butyl phenol), triethylene glycol-bis-[3-(3-tert-butyl-5-methyl-4-hydroxyphenyl) propionate], pentaerythritol-tetrakis(3-(3,5-di-tert-butyl-4-hydroxyphenyl) propionate], octadecyl-3-(3,5-di-tert-butyl-4-hydroxyphenyl) propionate, 2,2-thio-diethylenebis [3-(3,5-di-tert-butyl-4-hydroxyphenyl) propionate], 1,6-hexane diol-bis[3-(3,5-di-tert-butyl-4-hydroxyphenyl) propionate], tris-(3,5-di-tort-butyl-4-hydroxybenzyl)-isocyanurate, 1,3,5-trimethyl-2,4,6-tris(3,5-di-tert-butyl-4-hydroxybenzyl) benzene, N',N'-hexamethylenebis(3,5-di-tert-butyl-4-hydroxyhydrocinnamide), and 3,5-di-tert-butyl-4-hydroxybenzylphosphonate-diethyl ester may be cited.

Among other hindered phenols enumerated above, 2,4-dimethyl-6-tert-butyl phenol, 4-tert-butyl catechol, 2,5-di-tert-butyl hydroquinone, 2-tert-dibutyl hydroquinone, 4,4'-thio-bis(6-tert-butyl-m-cresol), 2,4-bis(n-octylthio)-6-(4-hydroxy-3,5-di-tert-butyl anilino)-1,3,5-triazine, 2,2'-thiobis-(4-methyl-6-tert-butyl phenol), and triethylene glycol-bis-[3-(3-tert-butyl-5-methyl-4-hydroxyphenyl) propionate] are advantageously used.

As typical examples of the phosphorous ester, triphenyl phosphite, tris(nonylphenyl)phosphite, triethyl phosphite, tris(2-ethylhexyl)phosphite, tridecyl phosphite, tris(tridecyl) phosphite, tristearyl phosphite, diphenyl mono(2-ethylhexyl) phosphite, diphenyl monodecyl phosphite, diphenyl monotridecyl phosphite, dilauryl hydrogen phosphite, dilauryl hydrogen phosphite, diphenyl hydrogen phosphite, tetraphenyl dipropylene glycol phosphite, tetraphenyl tetra(tridecyl)-pentaerythritol tetraphosphite, tetra (tridecyl)-4,4'-isopropylidene diphenyl phosphite, trilauryl trithiophosphite, bis(tridecyl)pentaerythritol diphosphite, bis(nonylphenyl) pentaerythritol phosphite, distearyl pentaerythritol diphosphite, tris(2,4-di-tert-butyl-phenyl) phosphite, hydrogenated bisphenol A-pentaerythritol phosphite polymer, and hydrogenated bisphenol A-phosphite polymer may be cited.

As typical examples of the phosphoric ester, phosphine and phosphoric acid amide, ethyldiethyl phosphonoacetate, ethyl acid phosphate, β-chloroethyl acid phosphate, butyl acid phosphate, butyl pyrophosphate, butoxyethyl acid phosphate, 2-ethylhexyl acid phosphate, di(2-ethylhexyl) phosphate, ethylene glycol acid phosphate, (2-hydroxyethyl) methacrylate acid phosphate, tris (2-chloroethyl) phosphate, tris(dichloropropyl)phosphate, octyl dichloropropyl phosphate, phenyldichloropropyl phosphate, trimethyl phosphate, triethyl phosphate, tributyl phosphate, trioctyl phosphate, tricresyl phosphate, triphenyl phosphate, triethyl phosiphine, tri-n-butyl phosphine, tricyclohexyl phosphine, triphenyl phosphine, and hexamethyl phosphoric triamide may be cited.

Among other phosphorous esters, phosphoric esters, phosphine, and phosphoric acid amides enumerated above, tris(nonylphenyl) phosphate, distearyl pentaerythritol diphosphite, tristearyl phosphite, and di {2-ethylhexyl} phosphate are advantageously used.

The amount of at least one member selected from the group consisting of the alkyl-substituted hydroxy benzenes and hindered phenols mentioned above to be used is in the range of 0.0001 to 1% by weight, preferably 0.001 to 0.1% by weight, based on the amount of the maleimide. The amount of at least one member selected from the group consisting of phosphorous esters, phosphoric esters, phosphine, and phosphoric acid amides mentioned above to be used is in the range of 0.0001 to 0.1 by weight, preferably 0.001 to 0.1% by weight, based on the amount of the maleimide. When at least one member selected from the group consisting of alkyl-substituted hydroxy benzenes and hindered phenols is used in combination with at least one member selected from the group consisting of phosphorous esters, phosphoric esters, phosphine, and phosphoric acid amides, the ratio of combination of the two members is not particularly limited. It may be properly decided so that the amounts of the two members involved fall in the relevant ranges of use mentioned above.

Among the combinations between at least one member selected from the group consisting of alkyl-substituted hydroxy benzenes and hindered phenols and at least one member selected from the group consisting of phosphorous esters, phosphoric esters, phosphine, and phosphoric acid amides, the following combinations are particularly advantageous.

4-Tert-butyl catechol and distearyl pentaerythritol diphospite,

Triethylene glycol-bis[3-(3-tert-butyl-5-methyl-4-hydroxyphenyl)propionate] and distearyl pentaerythritol diphosphite, 4-Tert-butyl catechol and tristearyl phosphite.

In Method A and Method B mentioned above, the discoloration of the acrylonitrile solution of maleimide can be effectively prevented by adjusting the molecular oxygen concentration of the gaseous phase part of the acrylonitrile solution (providing that the molecular oxygen concentration is obtained of the gas mixture excluding maleimide and acrylonitrile on the basis of volume; this remark similarly applies hereinafter) to a level in the range of 0.01 to 10% by volume.

A deviation from the range mentioned above is unfavorable because the discoloration will not be effectively precluded if the molecular oxygen concentration exceeds 10% by volume and the acrylonitrile solution of maleimide will suffer inclusion of monomers other than maleimide and acrylonitrile and incur discoloration owing to the contamination of containers such as storage tanks if the molecular oxygen concentration is less than 0.01% by volume. It is, therefore, appropriate that the molecular oxygen concentration is in the range of 0.01 to 10% by volume, preferably 0.1 to 8% by volume, and more preferably 1 to 7% by volume. The gas mixture excluding maleimide and acrylonitrile mentioned above generally comprises molecular oxygen and such inert gases as nitrogen, carbon dioxide, helium, and argon. Since nitrogen is advantageously used as the inert gas, the gas mixture consisting of molecular oxygen and nitrogen may be cited as an appropriate example of the gas mixture excluding maleimide and acrylonitrile.

Now, other preferred embodiments of Method A and Method B will be cited below.

(a) The water content in the acrylonitrile solution is lowered to a level of not more than 0.3% by weight and, at the same time, the molecular oxygen concentration in the gaseous phase part of the acrylonitrile solution is adjusted to a level in the range of 0.01 to 10% by volume (refer to Example 13).

(b) The water content in the acrylonitrile solution is lowered to a level of not more than 0.3% by weight, at least one member selected from the group consisting of alkyl-substituted hydroxy benzenes and hindered phenols or at least one member selected from the group consisting of phosphorous esters, phosphoric esters, phosphine, and phosphoric acid amides is allowed to exist in the acrylonitrile solution, and the molecular oxygen concentration in the gaseous phase part of the acrylonitrile solution is adjusted to a level in the range of 0.01 to 10% by volume (refer to Example 10).

(c) The water content in the acrylonitrile solution is lowered to a level of not more than 0.3% by weight, at least one member selected from the group consisting of alkyl-substituted hydroxy benzenes and hindered phenols and at least one never selected from the group consisting of phosphorous esters, phosphoric esters, phosphine, and phosphoric acid amides are allowed to exist in the acrylonitrile solution, and the molecular oxygen concentration in the gaseous phase part of the acrylonitrile solution is adjusted to a level in the range of 0.01 to 10% by volume (refer to Examples 1, 2, 3, and 6).

In the embodiments (a) to (c) mentioned above, the discoloration by aging of the acrylonitrile solution can be diminished to a lower level by lowering the water content in the acrylonitrile solution to a level of not more than 0.2% by weight, preferably 0.1% by weight. Particularly, the acrylonitrile solution whose values of $\Delta L$, $\Delta a$, and $\Delta b$ are respectively not more than 1, not more than 1, and not more than 2 can be prepared by lowering the water content in the acrylonitrile solution to a level of not more than 0.05% by weight.

Further in Method A and Method B mentioned above, the discoloration of the acrylonitrile solution can be diminished more effectively by allowing a metal-inactivating agent to exist in the acrylonitrile solution.

As typical examples of the metal-inactivating agent mentioned above, N,N'-bis[3-(3,5-di-tert-butyl-4-hydroxyphenyl) propionyl] hydrazine, 2,2'-oxamide bis (ethyl-3-(3,5-di-tert-butyl-4-hydroxyphenyl)propionatel, N,N'-disalicylidene-1,2-propane diamine, benzotriazole, tollyl triazole, tollyl triazole-potassium salt, and mercapto benzotriazole-sodium salt may be cited. Among other metal-inactivating agents enumerated above, N,N'-bis[3-(3,5-di-tert-butyl-4-hydroxyphenyl) propionyl] hydrazine, and 2,2'-oxamide bis[ethyl-3-(3,5-di-tert-butyl-4-hydroxyphenyl) propionate] are advantageously used. These metal-inactivating agents may be used either singly or in the form of a mixture of two or more members. The amount of the metal-inactivating agent to be added is in the range of 0.0001 to 1% by weight, preferably 0.001 to 0.1% by weight. As concrete means to implement the addition of the metal-inactivating agent, the following embodiments may be cited.

(a) The water content in the acrylonitrile solution is lowered to a level of not more than 0.1% by weight and the metal-inactivating gent is added (refer to Example 14).

(b) The water content in the acrylonitrile solution is lowered to a level or not more than 0.1% by weight, the molecular oxygen concentration of the gaseous phase part of the acrylonitrile solution is adjusted to a level in the range of 0.01 to 10% by volume, and the metal-inactivating agent is added (refer to Example 15).

(c) At least one member selected from the group consisting of alkyl-substituted hydroxy benzenes and hindered phenols and at least one member selected from the group consisting of phosphorous esters, phosphoric esters, phosphine, and phosphoric acid amides are caused to exist in the acrylonitrile solution and the metal-inactivating agent is added (refer to Example 4).

(d) The water content in the acrylonitrile solution is lowered to a level of not more than 0.3% by weight, at least one member selected from the group consisting of alkyl-substituted hydroxy benzenes and hindered phenols or at least one member selected from the group consisting of phosphorous esters, phosphoric esters, phosphine, and phosphoric acid amides is caused to exist in the acrylonitrile solution, and the metal-inactivating agent is added (refer to Example 14).

(e) At least one member selected from the group consisting of alkyl-substituted hydroxy benzenes and hindered phenols and at least one member selected from the group consisting of phosphorous esters, phosphoric esters, phosphine, and phosphoric acid amides are caused to exist in the acrylonitrile solution, the molecular oxygen concentration of the gaseous phase part of the acrylonitrile solution is adjusted to a level in the range of 0.01 to 10% by volume, and the metal-inactivating agent is added (refer to Examples 5, 7, and 8).

(f) The water content in the acrylonitrile solution is lowered to a level of not more than 0.3% by weight, at least one member selected from the group consisting of alkyl-substituted hydroxy benzenes and hindered phenols or at least one member selected from the group consisting of phosphorous esters, phosphoric esters, phosphine, and phosphoric acid amides is caused to exist in the acrylonitrile solution, the molecular oxygen concentration of the gaseous phase part of the acrylonitrile solution is adjusted to a level in the range of 0.01 to 10% by volume, and the metal-inactivating agent is added (refer to Example 17).

In the embodiments (a) to (f) mentioned above, the acrylonitrile solution whose values of ΔL, Δa, and Δb are respectively not more than 1, not more than 1, and not more than 2 can be prepared by lowering the water content in the acrylonitrile solution to a level of not more than 0.05% by weight.

The acrylonitrile solution of N-phenyl maleimide of this invention whose total content of AZB and DPH is not more than 500 ppm (based on the weight of the acrylonitrile solution) is used advantageously for the production of an acrylonitrile based copolymer, specifically an acrylonitrile-N-phenyl maleimide-containing copolymer, which precludes coloration and excels in color characteristics. The acrylonitrile solution of N-phenyl maleimide whose total content of AZB and DPH is not more than 100 ppm is appropriate in particular. Preferably, the total content of AZB and DPH in the acrylonitrile solution is as low as possible. Depending on the application for which the acrylonitrile solution is intended, it suffices to adjust the total content to the neighborhood of 20 ppm.

The acrylonitrile solution of N-phenyl maleimide whose total content of AZB and DPH is not more than 500 ppm, preferably not more than 100 ppm, can be prepared by adopting without any modification the method which is used for the preparation of the acrylonitrile solution of maleimide whose values of ΔL, Δa, and Δb are respectively not more than 5, not more than 5, and not more than 10, preferably not more than 1, not more than 1, and not more than 2.

Now, Method C and Method D which are used particularly advantageously for the preparation of the acrylonitrile solution of maleimide of this invention whose values of ΔL, Δa, and Δb are respectively not more than 5, not more than 5, and not more than 10, preferably not more than 1, not more than 1, and not more than 2 will be described below.

By Method C and Method D, the acrylonitrile solution of maleimide which incurs absolutely no discoloration by aging or diminishes the discoloration appreciably can be easily prepared. In other words, these methods permit the acrylonitrile solution of maleimide appropriate for the production of an acrylonitrile based copolymer precluding coloration and excelling in color characteristics to be prepared by a simple procedure.

The maleimide to be used herein is not particularly limited. Any of the maleimides obtained by various known methods can be adopted as already pointed out.

Since the maleimide which is obtained by such a known method (occasionally containing an organic solvent used in the process of reaction) (hereinafter referred to as "crude maleimide") suffers such extraneous substances as, for example, phosphoric acid that has been used as an acid catalyst to remain therein, it is generally refined by such treatments as washing with water and distillation and converted into a finished maleimide. To be specific, the refinement may be implemented by a series of operations such as, for example, (1) a procedure of washing the crude maleimide with water thereby depriving it of the organic solvent and subsequently distilling the washed maleimide, (2) a procedure of treating the crude maleimide with such an inorganic acid as sulfuric acid, washing the acid-treated maleimide with water, and thereafter separating the organic solvent therefrom, and (3) washing the crude maleimide with water, recrystallizing the washed maleimide as by concentration, and subsequently separating the produced crystals by filtration.

According to Method C, the acrylonitrile solution of maleimide is obtained by causing the finished maleimide obtained in a molten state from the purifying process described above to allow the coexistence therein of a primary antioxidant and a secondary antioxidant, then cooling and solidifying the maleimide, and dissolving the maleimide in a solid state in acrylonitrile.

According to Method D, the acrylonitrile solution of maleimide is obtained by causing the finished maleimide obtained in a molten state from the purifying process described above to be dissolved in acrylonitrile in the presence of a primary antioxidant and a secondary antioxidant.

The term "primary antioxidant" mentioned above is generally defined as a radical chain inhibitor [refer, for example, to Ed. Sawatari et al. "Handbook on Antioxidants," (published by Taiseisha on Oct. 25, 1976)]. The phenol type antioxidants may be cited as representatives. As concrete examples of the primary antioxidant, the following compounds may be cited.

Phenol Types Antioxidant 2,4-Dimethyl-6-tert-butyl phenol, 4-tert-butyl catechol, 4,4'-thio-bis(6-tert-butyl-m-cresol), 2,4-bis(n-octylthio)-6-(4-hydroxy-3,5-di-tert-butyl anilino)-1,3,5-triazine, 2,2'-thiobis-(4-methyl-6-tert-butyl phenol), triethylene glycol-bis-[3-(3-tert-butyl-5-methyl-4-hydroxyphenyl)propionate], pentaerythritol-tetrakis[3-(3,5-di-tert-butyl-4-hydroxyphenyl)propionate], octadecyl-3-(3,5-di-tert-butyl-4-hydroxyphenyl)propionate, 2,2-thio-diethylenebis[3,(3,5-di-tert-butyl-4-hydroxyphenyl)propionate], 1,6-hexane diol-bis[3-(3,5di-tert-butyl-4-hydroxyphenyl)propionate], tris-(3,5-di-tert-butyl-4-hydroxybenzyl)-isocyanurate, 1,3,5-trimethyl-2,4,6-tris(3,5-di-tert-butyl-4-hydroxybenzyl) benzene, N,N'-hexamethylene bis(3,5-di)-tert-butyl-4-hydroxy-hydrocinnamite), and 3,5-di-tert-butyl-4-hydroxy-benzyl phosphonate-diethyl ester.

Among other primary antioxidants enumerated above, such alkyl-substituted hydroxy benzenes and/or hindered phenols as 2,4-dimethyl-6-tert-butyl phenol, 4-tert-butyl catechol, 4,4'-thio-bis(6-tert-butyl-m-cresol), 2,4-bis(n-octylthio)-6-(4-hydroxy-3,5-di-tert-butyl anilino)-1,3,5-triazine, 2,2'-thiobis-(4-methyl-6-tert-butyl phenol), and triethylene glycol-bis-[3-(3-tert-butyl-5-methyl-4-hydroxyphenyl)propionate] are used advantageously.

The term "secondary antioxidant" mentioned above is generally defined as a peroxide decomposing agent (refer, for example, to the "Handbook on Antioxidants" mentioned above). Sulfur type antioxidants and phosphorus type antioxidants are representative. The following compounds may be cited as typical examples of these secondary antioxidants.

Sulfur Type Antioxidants

Dioctyl-3,3'-thiodipropionate, dilauryl-3,3'-thiodipropionate, ditetradecyl-3,3'-thiodipropionate, distearyl-3,3'-thiodipropionate, laurylstearyl-3,3'-thiodipropionate, pentaerythritol tetrakis (β-laurylthiopropionate), ditridecyl-3,3'-thiodipropionate, 2-mercaptobenzoimidazole, and dilauryl sulfide.

Phosphorus Type Antioxidants

Phosphorous Esters

Triphenyl phosphite, tris(nonylphenyl) phosphite, triethyl phosphite, tris(2-ethylhexyl) phosphite, tridecyl phosphite, tris (tridecyl) phosphite, triatearyl phosphite, diphenylmono (2-ethylhexyl) phosphite, diphenyl monodecyl phosphite, diphenyl monotridecyl phosphite, dilauryl hydrogen phosphite, diphenyl ,hydrogen phosphite, tetraphenyl dipropylene glycol phosphate, tetraphenyltetra(tridecyl) pentaerythritol tetraphosphite, tetra (tridecyl)-4,4'-isopropylidene diphenyl phosphite, trilauryl trithiophosphite, bis(tridecyl) pentaerythritol diphosphite, bis (nonylphenyl) pentaerythritol diphosphite, distearyl pentaerythritol diphosphite, tris(2,4-di-tert-butylphenyl) phosphite, hydrogenated bisphenol A-pentaerythritol phosphite polymer, and hydrogenated bisphenol A-phosphite polymer.

Phosphoric Esters, Phosphine and Phosphoric Acid Amides

Ethyldiethyl phosphoroacetate, ethyl acid phosphate, β-chloroethyl acid phosphate, butyl acid phosphate, butyl pyrophosphate, butoxyethyl acid phosphate, 2-ethylhexyl acid phosphate, di(2-othylhexyl) phosphate, ethylene glycol acid phosphate, (2-hydroxyethyl)methacrylate acid phosphate, tris(2-chloroethyl) phosphate, tris (dichloropropyl) phosphate, octyl dichloropropyl phosphate, phenyldichloropropyl phosphate, trimethyl phosphate, triethyl phosphate, tributyl phosphate, trioctyl phosphate, tricresyl phosphate, triphenyl phosphate, triethyl phosphine, tri-n-butyl phosphine, tricyclohexyl phosphine, triphenyl phosphine and hexamethyl phosphoric triamide.

Among other phosphorus type antioxidants enumerated above, tris(nonylphenyl) phosphite, distearyl pentaerythritol diphosphite, tristearyl phosphite, and di (12-ethylhexyl) phosphate are advantageously used.

Particularly, the combination of 4-tert-butyl catechol with distearyl pentaerythritol diphosphite, the combination of triethylene glycol-bis[3-(3-tert-butyl-5-methyl-4-hydroxyphenyl)propionate] with distearyl pentaerythritol diphosphite, and the combination of 4-tert-butyl catechol with tristearyl phosphite are used appropriately.

The amount of the primary antioxidant to be allowed to exist in the finished maleimide is in the range of 0.0001 to 1% by weight, preferably 0.001 to 0. 1 by weight, based on the amount of the finished maleimide. The amount of the secondary antioxidant to be allowed to exist in the finished maleimide is in the range of 0.0001. to 1% by weight, preferably 0.001 to 0.1% by weight, based on the amount of the finished maleimide. The ratio of the amount of the primary antioxidant to that of the secondary antioxidant is not particularly limited. It may be properly decided so that the amounts of the two antioxidants fall in the relevant ranges of the amount of use mentioned above.

Now, Method C and Method D will be described in greater detail below.

Method C

This method, as described above, comprises causing the molten maleimide obtained by purifying crude maleimide to permit coexistence therein of a primary antioxidant and a secondary antioxidant, namely causing the finished maleimide derived in the molten state from the purifying step to permit coexistence therein of a primary antioxidant and a secondary antioxidant, then solidifying the molten maleimide, and dissolving the solidified maleimide in acrylonitrile. This method will be described below with reference to a case of performing distillation as one of the purifying steps.

The conditions for carrying out the distillation of maleimide have no particular restriction. The distillation can be carried out in accordance with the conventional method under the conventional conditions.

Incidentally, the distillation of maleimide is generally carried out in the presence of a polymerization inhibitor for the purpose of preventing the maleimide from being polymerized. Any of the known polymerization inhibitors can be used therefor. As typical examples of the polymerization inhibitor, methoxy benzoquinone, p-methoxyphenol, phenothiazine, hydroquinone, alkylated diphenyl amines, methylene blue, 4-tert-butyl catechol, 2,5-di-tert-butyl hydroquinone, zinc dimethyldithiocarbamate, dimethyl dithiocarbamic acid, copper dibutyl dithiocarbamate, copper salicylate, thiodipropionic esters, mercaptobenzimidazole, triphenyl phosphite, alkyl phenols, alkyl bisphenols, and hindered phenols may be cited.

The coexistence of the primary antioxidant and the secondary antioxidant in the molten maleimide is accomplished satisfactorily by simply adding the primary antioxidant and the secondary antioxidant to the maleimide obtained in a molten state in consequence of the treatment of distillation. The primary antioxidant and the second antioxidant may be added either simultaneously or separately from each other.

When they are added separately of each other, the order in which they are added is not critical. It is particularly appropriate to effect this addition of the primary antioxidant and the secondary antioxidant before the maleimide in the molten state is exposed to the ambient air excessively. Specifically, when the maleimide emanating in the molten state from the top of a distillation column is stored provisionally in a tank, then solidified, and dissolved in the solid state in acrylonitrile, it is advantageous to add the primary antioxidant and the second antioxidant to the maleimide in the molten state before it is put to the provisional storage. More preferably, the primary antioxidant and the secondary antioxidant are added quickly, and particularly immediately to the maleimide emanating in the molten state from the top of the distillation column.

Incidentally, when the primary antioxidant has the function of a polymerization inhibitor to be used during the purifying of crude maleimide by distillation and this polymerization inhibitor (primary antioxidant) remains in the molten maleimide emanating from the distillation column, it is no longer necessary to add the primary antioxidant anew and it suffices to add only the secondary antioxidant to the molten maleimide. Even in this case, it is of course possible to add (supplement) the primary antioxidant with a refill of the same kind or with a primary antioxidant of a different kind. As a typical example of the primary antioxidant which has the function of a polymerization inhibitor as described above, 4-tert-butyl catechol may be cited. The same remarks hold good for the secondary antioxidant.

The maleimide in the molten state which has permitted the primary antioxidant and the second antioxidant to coexist therein is solidified and molded in an arbitrary form such as powder, flakes, or tablets and the maleimide in the solid state is dissolved in acrylonitrile to produce the acrylonitrile solution of the maleimide.

The dissolution in acrylonitrile of the maleimide in the solid state it not always required to be immediately carried out. The solid maleimide, when necessary, may be dissolved in acrylonitrile after being stored for a prescribed length of time. One of the characteristic features of Method C resides in the fact that the acrylonitrile solution or maleimide which defies discoloration even after protracted handling can be prepared by dissolving in acrylonitrile the maleimide which has been stored in the solid state over a period of several months, for example.

Method D

This method, as described above, comprises causing the molten maleimide obtained by purifying crude maleimide to be dissolved in acrylonitrile in the presence of the primary antioxidant and the second antioxidant. This method, similarly to Method C mentioned above, will be described below with reference to a case of performing distillation as one of the purifying processes.

Since the distillation involved in this method is identical to that involved in Method C mentioned above, it will be omitted from the following description. One embodiment of this method comprises adding the primary antioxidant and the secondary antioxidant to the finished maleimide emanating in the molten state from the top of the distillation tower thereby effecting coexistence of the antioxidants in the molten maleimide and then dissolving the molten maleimide in acrylonitrile before being solidified. The coexistence of the primary antioxidant and the secondary antioxidant according to this embodiment can be attained in the same manner as in Method C mentioned above. When such a primary antioxidant as 4-tert-butyl catechol is used, for example, this primary antioxidant may be used as a polymerization inhibitor during the process of distillation and then the secondary antioxidant or, when necessary, both the primary antioxidant and the second antioxidant may be added to the molten maleimide resulting from the distillation for the purpose of the coexistence. In this embodiment, similarly to Method C mentioned above, it is appropriate to add the primary antioxidant and the secondary antioxidant quickly to the molten maleimide emanating from the top of the distillation column.

Another embodiment of Method D comprises either adding the finished maleimide emanating in the molten state from the top of the distillation column simultaneously with the primary antioxidant and the secondary antioxidant to acrylonitrile and dissolving them therein or dissolving the molten maleimide in acrylonitrile having the primary antioxidant and the second antioxidant added in advance thereto. In the case of this embodiment, it is appropriate to have the molten maleimide quickly dissolved in acrylonitrile.

As the acrylonitrile to be used in implementing Method C and Method D, the industry grade acrylonitrile proves appropriate. Generally, the industry grade acrylonitrile contains a small amount of water and this water is thought to constitute a factor for causing the acrylonitrile solution of maleimide to produce a substance responsible for coloration. These methods can use the industry grade acrylonitrile without any trouble. Method C and Method D, therefore, are at a great economic advantage in allowing production of the acrylonitrile solution incurring absolutely no discoloration or appreciably diminished discoloration by aging even by using the industry grade acrylonitrile as the solvent.

In these methods as in Method A and Method B mentioned above, the discoloration of the acrylonitrile solution by aging can be effectively diminished by lowering the molecular oxygen concentration in the gaseous phase part of the acrylonitrile solution in the process of handling (providing that the molecular oxygen concentration is obtained of the gas mixture excluding maleimide and acrylonitrile on the basis of volume) to a level of not more than 10% by volume, preferably in the range of 0.1 to 8% by volume, and more preferably in the range of 1 to 7% by volume.

The gas mixture excluding maleimide and acrylonitrile mentioned above generally comprises molecular oxygen and such inert gases as nitrogen, carbon dioxide, helium, and argon. Since nitrogen is particularly advantageously used as the inert gas, the gas mixture comprising molecular oxygen and nitrogen may be cited as an appropriate example of the gas mixture excluding maleimide and acrylonitrile.

The discoloration of the acrylonitrile solution by aging can be more effectively diminished by allowing the same metal-inactivating agent as mentioned in Method A and Method B to coexist together with the primary antioxidant and the secondary antioxidant in the molten maleimide. The metal-inactivating agent and the amount of addition thereof are the same as those already mentioned in the description of Method A and Method B. This metal-inactivating agent may be added to the acrylonitrile solution of maleimide which has been prepared in accordance with Method C or Method D.

One preferred embodiment of Method C and Method D, therefore, is as follows.

(a) The acrylonitrile solution of maleimide is prepared in accordance with Method C or Method D and the molecular oxygen concentration of the gaseous phase part of this acrylonitrile solution is adjusted to a level of not more than 10% by volume, preferably in the range of 0.1 to 8% by volume, and more preferably in the range of 1 to 7% by volume.

In accordance with Method C and Method D mentioned above, the acrylonitrile solution of maleimide incurring absolutely no discoloration or appreciably diminished discoloration by aging can be prepared conveniently and easily.

Method C and Method D mentioned above are used particularly advantageously for the preparation of the acrylonitrile solution of N-phenyl maleimide whose total content of AZB and DPH is not more than 500 ppn, particularly not more than 100 ppm.

The acrylonitrile solution of maleimide of this invention enjoys transparency and appreciably diminished discoloration. The use of this acrylonitrile solution of maleimide, therefore, permits the production of an acrylonitrile based copolymer, an acrylonitrile-maleimide-containing copolymer to be exact, which precludes coloration and excels in color characteristics. By the same token, the use or the acrylonitrile solution of N-phenyl maleimide of this invention whose total content of AZB and DPH is not more than 500 ppm permits the production of an acrylonitrile based copolymer, an acrylonitrile-N-phenyl maleimide-containing copolymer to be exact, which precludes coloration and excels in color characteristics.

The term "acrylonitrile based copolymer" as used in this invention refers to copolymers which are obtained by the use of the acrylonitrile solution of maleimide mentioned above (including the acrylonitrile solution of N-phenyl maleimide mentioned above). The term embraces copolymers of maleimides with acrylonitrile, and copolymers of maleimides with acrylonitrile and monomers which are copolymerizable therewith.

As representative compounds of the copolymerizable monomer, methacrylic esters such as, for example, methyl methacrylate, ethyl methacrylate, propyl methacrylate, cyclohexyl methacrylate, and isobonyl methacrylate; acrylic esters such as, for example, methyl acrylate, ethyl acrylate, propyl acrylate, and butyl acrylate; aromatic vinyl compounds such as, for example, styrene and α-methyl styrene; and conjugate dienes such as, for example, butadiene may be cited. Among other copolymerizable monomers enumerated above, methyl methacrylate, methyl acrylate, styrene, and α-methyl styrene prove advantageous in exhibiting excellent reactivity and permitting the production of resins which excel in heat-resistance.

As other concrete examples of the copolymer mentioned above, acrylonitrile-butadiene-styrene (ADS) resin, acrylonitrile-acrylic rubber-styrene (AAS) resin, and acrylonitrile-chlorinated polyethylene-styrene (ACS) resin which contain maleimide as one component of copolymer may be cited.

The acrylonitrile based copolymers of this invention are invariably known to the art. They can be easily produced by the known method of polymerization except that the acrylonitrile solution of maleimide of this invention is used in place of the known acrylonitrile solution of maleimide. These acrylonitrile based copolymers, when necessary, can incorporate therein various known additives.

Now, this invention will be described more specifically below with reference to working examples and controls.

EXAMPLE 1 OF SYNTHESIS

Synthesis of N-phenyl Maleimide

An N-phenyl maleamic acid obtained from aniline and maleic anhydride was left reacting in an o-xylene solvent at a temperature of not less than 130° C. in the presence of an acid catalyst. The reaction was allowed to proceed while the water formed thereby was expelled in the form of a mixture with o-xylene from the system by distillation. The reaction mixture obtained by the resultant ring-closure conversion into imide was separated into an organic solvent layer containing therein N-phenyl maleimide and a catalyst layer. The organic solvent layer was washed with water. The organic solvent layer thus obtained was distilled under a reduced pressure to expel o-xylene. The residue by the distillation was further distilled to obtain a yellow N-phenyl maleimide. This product, on analysis by liquid chromatography, was found to have a purity of not less than 99.5%.

EXAMPLE 1

Two Pyrax test tubes with a size of 18 mm in inside diameter and 180 in height, were prepared.

In each of the test tubes, an acrylonitrile solution having an N-phenyl maleimide concentration of 60% by weight, a water content of 0.1% by weight, an antioxidant (a-1) content of 500 ppm (based on N-phenyl maleimide; which similarly applies hereinafter) and an antioxidant (b-1) content of 500 ppm was prepared by dissolving 9 g of the N-phenyl maleimide obtained in Example 1 of Synthesis in 6 g of acrylonitrile having a water content of 0.005% by weight, then adding 4.5 mg of pentaerythritol-tetrakis[3-(3, 5-di-tert-butyl-4-hydroxyphenyl) propionate] [antioxidant (a-1)] and 4.5 mg of tristearyl phosphite [antioxidant (b-1)] to the resultant solution, and adjusting the water content of the produced mixture.

When the acrylonitrile solution in one of the test tubes was tested for the L, a, and b values after the preparation, L=99.3, a=21.0, and b=39.0 were obtained. The other test tube, with the gaseous phase part of the acrylonitrile solution displaced with nitrogen gas containing 7% by volume of molecular oxygen, was used for the forced coloration test contemplated by this invention. After 3 days' (72 hours') standing, the test piece was extracted from the test tube and the acrylonitrile solution left in the test tube was measured for the L, a, and b values. The results were L=98.6, a=19.8, and b=41.2 and the differences in the L, a, and b values before and after the test were ΔL=0.7, Δa=1.2, and Δb=2.2. The solution after the test was transparent. The results are shown in Table 1.

EXAMPLE 2

An acrylonitrile solution shown in Table 1 was prepared by following the procedure of Example 1 while using triethylene glycol-bis[3-(3-tert-butyl-5-methyl-4-hydroxyphenyl)propionate] [antioxidant (a-2)] and tris-nonylphenyl phosphate [antioxidant (b-2)] instead as antioxidants. The acrylonitrile solution was tested to determine the L, a, and b values and the differences of the L, a, and b values before and after the test in the same manner as in Example 1. The results are shown in Table 1.

EXAMPLE 3

An acrylonitrile solution shown in Table 1 was prepared by following the procedure of Example 1 while using octadecyl-3-(3,5-di-tert-butyl-4-hydroxyphenyl)propionate [antioxidant (a-3)] and distearyl pentaerythritol diphosphite [antioxidant (b-3)] instead as antioxidants. The acrylonitrile solution was tested to determine the L, a, and b values and the differences of the L, a, and b values before and after the test in the same manner as in Example 1. The results are shown in Table 1.

EXAMPLE 4

An acrylonitrile solution shown in Table 1 was prepared by following 4-tert-butyl catechol [antioxidant (a-4)] and distearyl pentaerythritol diphosphite [antioxidant (b-3)] instead as antioxidants and further using N,N'-bis[3-(3,5-di-tert-butyl-4-hydroxyphenyl)propionyl] hydrazine [inactivating agent (c-1)] as a metal-inactivating agent. The acrylonitrile solution was tested to determine the L, a, and b values and the differences of the L, a, and b values before and after the test in the same manner as in Example 1. The results are shown in Table 1.

EXAMPLE 5

An acrylonitrile solution shown in Table 1 was prepared by following the procedure of Example 1 while using triethylene glycol-bis[3-(3-tert-butyl-5-methyl-4-hydroxyphenyl)propionate] [antioxidant (a-2)] and distearyl pentaerythritol diphosphite [antioxidant (b-3)] instead as antioxidants and further using 2,2'-oxamide-bis[ethyl-3-(3,5-di-tert-butyl-4-hydroxyphenyl)propionate] [inactivating agent (c-2)] as a metal-inactivating agent. The acrylonitrile solution was tested to determine the L, a, and b values and the differences of the L, a, and b values before and after the test in the same manner as in Example 1. The results are shown in Table 1.

TABLE 1

| Example | 1 | 2 | 3 | 4 | 5 |
|---|---|---|---|---|---|
| Antioxidant | | | | | |
| Kind | a - 1 | a - 2 | a - 3 | a - 4 | a - 2 |
| Amount added | 500 | 500 | 1000 | 100 | 1000 |
| Kind | b - 1 | b - 2 | b - 3 | b - 3 | b - 3 |
| Amount added | 500 | 500 | 1000 | 1000 | 1000 |
| Metal-inactivating agent | | | | | |
| Kind | — | — | — | c - 1 | c - 2 |
| Amount added | | | | 500 | 1000 |
| Water content in solution | 0.1 | 0.2 | 0.2 | 0.1 | 0.2 |
| Molecular oxygen concentration | 7 | 7 | 7 | 21 | 5 |
| Clarity of solution after test | transparent | transparent | transparent | transparent | transparent |
| L, a, and b values | | | | | |
| L | 99.3 | 99.3 | 99.3 | 99.3 | 99.3 |
| a | −21.3 | −21.3 | −21.3 | −21.3 | −21.3 |
| b | 39.0 | 39.0 | 39.0 | 39.0 | 39.0 |
| Difference before and after test | | | | | |
| ΔL | 0.7 | 0.8 | 0.5 | 0.5 | 0.4 |
| Δa | 1.2 | 2.8 | 0.6 | 1.2 | 0.5 |
| Δb | 2.2 | 3.5 | 1.9 | 2.9 | 1.0 |

Amount of addition or antioxidant and metal-inactivating agent: ppm (based on N-phenyl maleimide)
Water content in solution: % by weight
Molecular oxygen concentration: % by volume (in gaseous phase part)
(a-1): Pentaerythrityl-tetrakis[3-(3,5-di-tert-butyl-4-hydroxyphenyl)propionate]
(a-2): Triethylene glycol-bis(3-(3-tert-butyl-5-methyl-4-hydroxyphenyl)propionate]
(a-3): Octadecyl-3-(3,5-di-tert-butyl-4-hydroxyphenyl)propionate
(a-4): 4-Tert-butyl catechol
(b-1): Tristearyl phosphite
(b-2): Trisnonylphenyl phosphite
(b-3): Distearyl pentaerythritol ciphosphite
(c-1): N,N'-bis[3-(3,5-di-tert-butyl-4-hydroxyphenyl)propionyl]hydrazine
(c-2): 2,2'-Oxamide bis[ethyl-3-(3,5-di-tert-butyl-4-hydroxyphenyl)propionate]

EXAMPLE 6

An acrylonitrile solution shown in Table 2 was prepared by following the procedure of Example 1 while using 4-tert-butyl catechol [antioxidant (a-4)] and di(2-ethylhexyl) phosphate [antioxidant (b-4)] instead as antioxidants. The acrylonitrile solution was tested to determine the L, a, and b values and the differences of the L, a, and b values before and after the test in the same manner as in Example 1. The results are shown in Table 2.

EXAMPLE 7

An acrylonitrile solution shown in Table 2 was prepared by following the procedure of Example 1 while using triethylene glycol-bis[3-(3-tert-butyl-5-methyl-4-hydroxyphenyl)propionate] [antioxidant (a-2)] and distearyl pentaerythritol diphosphite [antioxidant (b-3)] instead as antioxidants and 2,2'-oxamide bis[ethyl-3-(3,5-di-tert-butyl-4-hydroxyphenyl)propionate] [inactivating agent (c-2)] as a metal-inactivating agent. The acrylonitrile solution was tested to determine the L, a, and b values and the differences of the L, a, and b values before and after the test in the same manner as in Example 1. The results are shown in Table 2.

EXAMPLE 8

An acrylonitrile solution shown in Table 2 was prepared by following the procedure of Example 1 while using triethylene glycol-bis[3-(3-tert-butyl-5-methyl-4-hydroxyphenyl)propionate] [antioxidant (a-2)] and distearyl pentaerythritol diphosphite [antioxidant (b-3)] instead as antioxidants and 2,2'-oxamide bis[ethyl-3-(3,5-di-tert-butyl-4-hydroxyphenyl)propionate] [inactivating agent (c-2)] as a metal-inactivating agent. The acrylonitrile solution was tested to determine the L, a, and b values and the differences of the L, a, and b values before and after the test in the same manner as in Example 1. The results are shown in Table 2.

EXAMPLE 9

An acrylonitrile solution shown in Table 2 was prepared by following the procedure of Example 1. The acrylonitrile solution was tested to determine the L, a, and b values and the differences of the L, a, and b values before and after the test in the same manner as in Example 1. The results are shown in Table 2.

EXAMPLE 10

An acrylonitrile solution shown in Table 2 was prepared by following the procedure of Example 1 while using 1,6-hexanediol-bis[3-(3,5-di-tert-butyl-4-hydroxyphenyl)propionate] [antioxidant (a-5)] instead as antioxidants. The acrylonitrile solution was tested to determine the L, a, and b values and the differences of the L, a, and b values before and after the test in the same manner as in Example 1. The results are shown in Table 2

TABLE 2

| Example | 6 | 7 | 8 | 9 | 10 |
|---|---|---|---|---|---|
| Antioxidant | | | | | |
| Kind | a - 4 | a - 2 | a - 2 | — | a - 5 |
| Amount added | 100 | 1000 | 1000 | - | 1000 |
| Kind | b - 4 | b - 3 | b - 3 | — | — |
| Amount added | 1000 | 1000 | 1000 | | |
| Metal-inactivating agent | | | | | |
| Kind | — | c - 2 | c - 2 | — | — |
| Amount added | | 1000 | 500 | | |
| Water content in solution | 0.18 | 0.05 | 0.002 | 0.02 | 0.2 |
| Molecular oxygen concentration | 5 | 5 | 5 | 21 | 5 |
| Clarity of solution after test | transparent | transparent | transparent | transparent | transparent |

TABLE 2-continued

| Example | 6 | 7 | 8 | 9 | 10 |
|---|---|---|---|---|---|
| L, a, and b values | | | | | |
| L | 99.3 | 99.3 | 99.3 | 99.3 | 99.3 |
| a | −21.0 | −21.0 | −21.0 | −21.0 | −21.0 |
| b | 39.0 | 39.0 | 39.0 | 39.0 | 39.0 |
| Difference before and after test | | | | | |
| ΔL | 0.5 | 0.3 | 0.1 | 0.7 | 1.2 |
| Δa | 1.2 | 0.3 | 0.1 | 1.5 | 1.0 |
| Δb | 1.5 | 0.5 | 0.3 | 3.5 | 2.4 |

(a-5): 1,6-Hexanediol-bis[3-(3,5-di-tert-butyl-4-hydroxyphenyl)propionate]
(b-4): Di(2-ethylhexyl) phosphate
The other agents are the same as those shown in Table 1.

EXAMPLE 11

An acrylonitrile solution shown in Table 3 was prepared by following the procedure of Example 1 while using triethylene glycol-bis[3-(3-tert-butyl-5-methyl-4-hydroxyphenyl)propionate] [antioxidant (a-2)] and distearyl pentaerythritol diphosphite [antioxidant (b-3)] instead as antioxidants. The acrylonitrile solution was tested to determine the L, a, and b values and the differences of the L, a, and b values before and after the test in the same manner as in Example 1. The results are shown in Table 3.

EXAMPLE 12

An acrylonitrile solution shown in Table 3 was prepared by following the procedure of Example 1 while using distearyl pentaerythritol diphosphite [antioxidant (b-3)] instead as antioxidants. The acrylonitrile solution was tested to determine the L, a, and b values and the differences of the L, a, and b values before and after the test in the same manner as in Example 1. The results are shown in Table 3.

EXAMPLE 13

An acrylonitrile solution shown in Table 3 was prepared by following the procedure of Example 1. The acrylonitrile solution was tested to determine the L, a, and b values and the differences of the L, a, and b values before and after the test in the same manner as in Example 1. The results are shown in Table 3.

EXAMPLE 14

An acrylonitrile solution shown in Table 3 was prepared by following the procedure of Example 1 while using 2,2'-oxamide bis[ethyl-3-(3,5-di-tert-butyl-4-hydroxyphenyl)propionate] [inactivating agent (c-2)] as a metal-inactivating agent. The acrylonitrile solution was tested to determine the L, a, and b values and the differences of the L, a, and b values before and after the test in the same manner as in Example 1. The results are shown in Table 3.

EXAMPLE 15

An acrylonitrile solution shown in Table 3 was prepared by following the procedure of Example 1 while using 2,2'-oxamide bis[ethyl-3-(3,5-di-tert-butyl-4-hydroxyphenyl)propionate] [inactivating agent (c-2)] as a metal-inactivating agent. The acrylonitrile solution was tested to determine the L, a, and b values and the differences of the L, a, and b values before and after the test in the same manner as in Example 1. The results are shown in Table 3.

TABLE 3

| Example | 11 | 12 | 13 | 14 | 15 |
|---|---|---|---|---|---|
| Antioxidant | | | | | |
| Kind | a - 2 | — | — | — | — |
| Amount added | 1000 | | | | |
| Kind | b - 3 | b - 3 | — | — | — |
| Amount added | 500 | 1000 | | | |
| Metal-inactivating agent | | | | | |
| Kind | — | — | — | c - 2 | c - 2 |
| Amount added | | | | 500 | 500 |
| Water content in solution | 0.2 | 0.2 | 0.005 | 0.05 | 0.01 |
| Molecular oxygen concentration | 21 | 21 | 5 | 21 | 7 |
| Clarity of solution after test | transparent | transparent | transparent | transparent | transparent |
| L, a, and b values | | | | | |
| L | 99.3 | 99.3 | 99.3 | 99.3 | 99.3 |
| a | −21.0 | −21.0 | −21.0 | −21.0 | −21.0 |
| b | 39.0 | 39.0 | 39.0 | 39.0 | 39.0 |
| Difference before and after test | | | | | |
| ΔL | 0.8 | 1.0 | 0.8 | 0.7 | 0.3 |
| Δa | 1.3 | 1.6 | 0.5 | 0.9 | 0.5 |
| Δb | 2.5 | 3.6 | 1.8 | 1.7 | 1.2 |

The symbols and the like are the same as those of Table 1.

EXAMPLE 16

An acrylonitrile solution shown in Table 4 was prepared by following the procedure of Example 1 while using di (2-ethylhexyl) phosphate [antioxidant (b-4)] instead as antioxidants and N,N'-bis[3-(3,5-di-tert-butyl-4-hydroxyphenyl)propionyl] hydrazine [inactivating agent (c-1)] as a metal-inactivating agent. The acrylonitrile solution was tested to determine the L, a, and b values and the differences of the L, a, and b values before and after the test in the same manner as in Example 1. The results are shown in Table 4.

EXAMPLE 17

An acrylonitrile solution shown in Table 4 was prepared by following the procedure of Example 1 while using distearyl pentaerythritol diphosphite [antioxidant (b-3)] instead as antioxidants and 2,2'-oxamide bis[ethyl-3-(3,5-di-tert-butyl-4-hydroxyphenyl)propionate] [inactivating agent (c-2)] as a metal-inactivating agent. The acrylonitrile solution was tested to determine the L, a, and b values and the differences of the L, a, and b values before and after the test in the same manner as in Example 1. The results are shown in Table 4.

Controls 1 to 3

Acrylonitrile solutions shown in Table 5 were prepared. The acrylonitrile solutions were tested to determine the L, a, and b values and the differences of the L, a, and b values before and after the test in the same manner as in Example 1. The results are shown in Table 5.

TABLE 4

| Example | 16 | 17 |
|---|---|---|
| Antioxidant | | |
| Kind | — | — |
| Amount added | | |
| Kind | b - 4 | b - 3 |
| Amount added | 1000 | 1000 |

TABLE 4-continued

| Example | 16 | 17 |
|---|---|---|
| Metal-inactivating agent | | |
| Kind | c - 1 | c - 2 |
| Amount added | 1000 | 500 |
| Water content in solution | 0.1 | 0.25 |
| Molecular oxygen concentration | 21 | 5 |
| Clarity of solution after test | transparent | transparent |
| L.a.b. values | | |
| L | 99.3 | 99.3 |
| a | −21.0 | −21.0 |
| b | 39.0 | 39.0 |
| Difference before and after test | | |
| ΔL | 0.8 | 0.7 |
| Δa | 1.0 | 1.5 |
| Δb | 2.4 | 2.9 |

The symbols and the like are the same as those shown in Table 1 and Table 2.

TABLE 5

| Control | 1 | 2 | 3 |
|---|---|---|---|
| Antioxidant | | | |
| Kind | — | — | — |
| Amount added | | | |
| Kind | — | — | — |
| Amount added | | | |
| Metal-inactivating agent | | | |
| Kind | — | — | — |
| Amount added | | | |
| Water content in solution | 0.15 | 0.2 | 0.8 |
| Molecular oxygen concentration | 21 | 5 | 5 |
| Clarity of solution after test | transparent | transparent | white cloudy |
| L.a.b. values | | | |
| L | 99.3 | 99.3 | 99.3 |
| a | −21.0 | −21.0 | −21.0 |
| b | 39.0 | 39.0 | 39.0 |
| Difference before and after test | | | |
| ΔL | 6.2 | 3.6 | 10.7 |
| Δa | 6.5 | 5.2 | 6.7 |
| Δb | 10.4 | 8.5 | 10.5 |

The symbols and the like are the same as those shown in Table 1.

EXAMPLE 18

In a four-neck flask having an inner volume of 1 liter and provided with a stirrer, a condenser, a nitrogen gas inlet tube, and a dropping funnel, 38.4 g of styrene and 269.3 g of toluene (both guaranteed reagents; produced by Wako Pure Chemical Industries, Ltd.) were placed and, after the subsequent thorough displacement of the gaseous phase part with nitrogen, heated to 90° C. To the resultant solution in the flask, a mixed solution comprising 172.7 g of the acrylonitrile solution of N-phenyl maleimide obtained in Example 4 and 54.3 g of toluene, 102.4 g of styrene, and a solution consisting of 0.26 g of benzoyl peroxide (produced by Nippon Oils & Fats Co., Ltd.) and 12.2 g of toluene were drip-fed through the dropping funnel over a period of 3 hours, with the inner temperature of the tube kept at 90° C. After the completion of this drip-feeding, the contents of the tube were continuously stirred for 1.5 hours.

Then, part of the reaction product was extracted, diluted with methylethyl ketone, and then reprecipitated in methanol by a standard technique. The polymer consequently precipitated was filtered and dried, subjected to the measurement with a melt indexer (produced by Techno Seven K.K. and marketed under product code of "Type L240"), heated at 240° C. for 4 hours, and then molded into strands. By visual observation, the strands of polymer were found to have a light yellow clear appearance.

Control 4

Strands of a polymer were obtained by following the procedure of Example 18 while using the acrylonitrile solution of N-phenyl maleimide obtained in Control 1 instead. The polymer had a yellow brown appearance and showed a clear sign of coloration.

EXAMPLE 19

An acrylonitrile solution was produced by following the procedure of Example 4 while changing the molecular oxygen concentration in the gaseous phase part of the acrylonitrile solution to 5% by volume. The acrylonitrile solution was tested to determine the L, a, and b values and the differences of the L, a, and b values before and after the test in the same manner as in Example 4. The results are shown in Table 6.

EXAMPLE 20

An acrylonitrile solution was produced by following the procedure of Example 9 while changing the molecular oxygen concentration in the gaseous phase part of the acrylonitrile solution to 5% by volume. The acrylonitrile solution was tested to determine the L, a, and b values and the differences of the L, a, and b values before and after the test in the same manner as in Example 9. The results are shown in Table 6.

EXAMPLE 21

An acrylonitrile solution was produced by following the procedure of Example 11 while changing the molecular oxygen concentration in the gaseous phase part of the acrylonitrile solution to 5% by volume. The acrylonitrile solution was tested to determine the L, a, and b values and the differences of the L, a, and b values before and after the test in the same manner as in Example 11. The results are shown in Table 6.

EXAMPLE 22

An acrylonitrile solution was produced by following the procedure of Example 12 while changing the molecular oxygen concentration in the gaseous phase part of the acrylonitrile solution to 5% by volume. The acrylonitrile solution was tested to determine the L, a, and b values and the differences of the L, a, and b values before and after the test in the same manner as in Example 12. The results are shown in Table 6.

EXAMPLE 23

An acrylonitrile solution was produced by following the procedure of Example 14 while changing the molecular oxygen concentration in the gaseous phase part of the acrylonitrile solution to 5% by volume. The acrylonitrile solution was tested to determine the L, a, and b values and the differences of the L, a, and b values before and after the test in the same manner as in Example 14. The results are shown in Table 6.

EXAMPLE 24

An acrylonitrile solution was produced by following the procedure of Example 16 while changing the molecular oxygen concentration in the gaseous phase part of the acrylonitrile solution to 5% by volume. The acrylonitrile solution was tested to determine the L, a, and b values and the differences of the L, a, and b values before and after the test in the same manner as in Example 16. The results are shown in Table 7.

Control 5

An acrylonitrile solution was produced by following the procedure of Control 1 while changing the molecular oxygen concentration in the gaseous phase part of the acrylonitrile solution to 7% by volume. The acrylonitrile solution was tested to determine the L, a, and b values and the differences of the L, a, and b values before and after the test in the same manner as in Control 1. The results are shown in Table 7.

TABLE 6

| Example | 19 | 20 | 21 | 22 | 23 |
|---|---|---|---|---|---|
| Antioxidant | | | | | |
| Kind | a - 4 | — | a - 2 | — | — |
| Amount added | 100 | | 1000 | | |
| Kind | b - 3 | — | b - 3 | b - 3 | — |
| Amount added | 1000 | | 500 | 1000 | |
| Metal-inactivating agent | | | | | |
| Kind | c - 1 | — | — | — | c - 2 |
| Amount added | 500 | | | | 500 |
| Water content in solution | 0.1 | 0.02 | 0.2 | 0.2 | 0.05 |
| Molecular oxygen concentration | 5 | 5 | 5 | 5 | 5 |
| Clarity of solution after test | transparent | transparent | transparent | transparent | transparent |
| L, a, and b values | | | | | |
| L | 99.3 | 99.3 | 99.3 | 99.3 | 99.3 |
| a | −21.0 | −21.0 | −21.0 | −21.0 | −21.0 |
| b | 39.0 | 39.0 | 39.0 | 39.0 | 39.0 |
| Difference before and after test | | | | | |
| ΔL | 0.4 | 0.8 | 0.7 | 1.0 | 0.6 |
| Δa | 0.4 | 1.2 | 1.2 | 1.4 | 0.7 |
| Δb | 0.9 | 2.6 | 2.1 | 3 2 | 1.5 |

The symbols and the like are the same as those shown in Table 1 and Table 2.

TABLE 7

| Example | 24 | Control 5 |
|---|---|---|
| Antioxidant | | |
| Kind | — | — |
| Amount added | | |
| Kind | b - 4 | — |
| Amount added | 1000 | |
| Metal-inactivating agent | | |
| Kind | c - 1 | — |
| Amount added | 1000 | |
| Water content in solution | 0.1 | 0.15 |
| Molecular oxygen concentration | 5 | 7 |
| Clarity of solution after test | transparent | transparent |
| L, a, and b values | | |
| ΔL | 99.3 | 99.3 |
| Δa | −21.0 | −21.0 |
| Δb | 39.0 | 39.0 |

TABLE 7-continued

| Example | 24 | Control 5 |
|---|---|---|
| Diffference before and after test | | |
| ΔL | 0.7 | 3.4 |
| Δa | 0.9 | 5.1 |
| Δb | 2.2 | 9.2 |

The symbols and the like are the same as those shown in Table 1 and Table 2.

EXAMPLE 25

In a Pyrex test tube of 18 mm in diameter, 9 g of N-phenyl maleimide (produced by Nippon Shokubai Co., Ltd.) was dissolved in 6 g of acrylonitrile (produced by Sumitomo Chemical Co., Ltd.) having a water content of 0.41%b by weight at 40° C. to prepare an acrylonitrile solution of 60% by weight of N-phenyl maleimide. An SUS test piece (10×50×2 mm) was placed in the acrylonitrile solution held in the test tube, tightly sealed in the test tube with a silicone rubber stopper as enveloped in an ambience of air, and stored at 55° C. for 30 days. The acrylonitrile solution was tested to determine the L, a, and b values and the differences of the L, a, and b values before and after the storage by the method for the determination of L, a, and b values mentioned above. The results are as follows.

Before storage: L=99.3, a=−21.4, b=39.9

After storage: L=97.9, a=−20.1, b=42.8

Difference: ΔL=1.4, Δa=1.3, Δb=2.9

The acrylonitrile solution mentioned above was distilled to expel acrylonitrile therefrom. When the residue, N-phenyl maleimide, was tested for the AZB and DPH contents by liquid chromatography, the total content thereof was found to be 120 ppm based on the weight of the acrylonitrile solution.

Control 6

The procedure of Example 25 was repeated except that the acrylonitrile solution was stored at 70° C. for 120 days instead of storing it at 55° C. for 30 days. The L, a, and b values and the differences thereof before and after the storage were as follows.

Before storage: L=99.3, a=−21.4, b=39.9

After storage: L=92.2, a=−10.6, b=59.5

Difference: ΔL=7.1, Δa=10.8, Δb=19.6

When the acrylonitrile solution was tested for the total content of AZB and DPH in the same manner as in Example 25, the total content was found to be 520 ppm.

It is noted from the results given above that when the total content of AZB and DPH in the acrylonitrile solution exceeded 500 ppm, the b value among the L, a, and b values exceeded 50 and the ΔL, Δa, and Δb respectively exceeded 5, 5, and 10, indicating that the acrylonitrile solution was conspicuously discolored.

EXAMPLE 26

The procedure of Example 25 was repeated excepting nitrogen as containing 70 by volume of molecular oxygen was blown into the acrylonitrile solution for thorough displacement of the trapped air and the gaseous phase part was packed with the same gas and then the acrylonitrile solution was tightly sealed with a silicone rubber stopper. The L, a, and b values and the differences thereof before and after the storage were as follows.

Before storage: L=99.3, a=−21.4, b=39.9

After storage: L=98.6, a=−20.8, b=41.7

Difference: ΔL=0.7, Δa=0.6, Δb 1.8

When the acrylonitrile solution was distilled to expel acrylonitrile therefrom and the residue, N-phenyl maleimide, was tested for the AZB and DHP contents by liquid chromatography, the total AZB and DPH content was found to be 35 ppm based on the weight of the acrylonitrile solution.

EXAMPLE 27

The procedure of Example 25 was repeated except that fresh molten N-phenyl maleimide was used, triethylene glycol-bis[3-(3-tert-butyl-5-methyl-4-hydroxyphenyl) propionate] and distearyl pentaerythritol diphosphite were added as antioxidants each in an amount of 1000 ppm (based on the weight of the N-phenyl maleimide), nitrogen gas containing 7% by volume of molecular oxygen was blown into the solution for thorough displacement of the entrapped air, and the gaseous phase part was filled with the same gas and then tightly sealed with a silicone rubber stopper. The L, a, and b values and the differences thereof before and after the storage were as follows.

Before storage: L=99.3, a=−21.4, b=39.9

After storage: L=99.0, a=−21.2, b=40.4

Difference: ΔL=0.3, Δa=0.2, Δb=0.5

When the acrylonitrile solution was distilled to expel acrylonitrile therefrom and the residue, N-phenyl maleimide, was tested for the AZB and DHP contents by liquid chromatography, the total AZB and DPH content was found to be 10 ppm based on the weight of the acrylonitrile solution.

EXAMPLE 28

The procedure of Example 25 was repeated except that fresh molten N-phenyl maleimide was used, the water content in the acrylonitrile solution was changed to 0.03% by weight, triethylene glycol-bis[3-(3-tert-butyl-5-methyl-4-hydroxyphenyl)propionate] and distearyl pentaerythritol diphosphite were added as antioxidants each in an amount of 1000 ppm (based on the weight of the N-phenyl maleimide), nitrogen gas containing 7% by volume of molecular oxygen was blown into the solution for thorough displacement of the entrapped air, and the gaseous phase part was filled with the same gas and then tightly sealed with a silicone rubber stopper. The L, a, and b values and the differences thereof before and after the storage were as follows.

Before storage: L=99.3, a=−21.4, b=39.9

After storage: L=99.1, a=−21.3, b=40.1

Difference: ΔL=0.2, Δa=0.1, Δb=0.2

When the acrylonitrile solution was distilled to expel acrylonitrile therefrom and the residue, N-phenyl maleimide, was tested for the AZB and DHP contents by liquid chromatography, the total AZB and DPH content was found to be 10 ppm based on the weight of the acrylonitrile solution.

EXAMPLE 29

The procedure of Example 25 was repeated except that fresh molten N-phenyl maleimide was used, triethylene glycol-bis[3-(3-tert-butyl-5-methyl-4-hydroxyphenyl) propionate] and distearyl pentaerythritol diphosphite were added as antioxidants each in an amount of 1000 ppm (based on the weight of the N-phenyl maleimide), nitrogen gas containing 7% by volume of molecular oxygen was blown into the solution for thorough displacement of the entrapped air, the gaseous phase part was filled with the same gas and then tightly sealed with a silicone rubber stopper, and the solution was stored at 70° C. for 120 days. The L, a, and b values and the differences thereof before and after the storage were as follows.

Before storage: L=99.3, a=−21.4, b=39.9

After storage: L=98.3, a=−20.1, b=42.6

Difference: ΔL=1.0, Δa=1.3, a b−2.7

When the acrylonitrile solution was distilled to expel acrylonitrile therefrom and the residue, N-phenyl maleimide, was tested for the AZB and DHP contents by liquid chromatography, the total AZB and DPH content was found to be 90 ppm based on the weight of the acrylonitrile solution.

EXAMPLE 30

In a flask provided with a stirrer, a condenser, a nitrogen gas inlet tube, and a dropping funnel, 30 parts by weight of styrene and 36.67 parts by weight of toluene (both guaranteed reagents; produced by Wako Pure Chemical Industries, Ltd.) and 0.016 part by weight of tert-butyl peroxyisopropyl carbonate (produced by Kayaku-Akzo K.K.) were placed and, after the subsequent thorough displacement of the entrapped air from the gaseous phase part with nitrogen, heated to 100° C. To the resultant solution in the flask, a solution of 10 parts by weight of N-phenyl maleimide in 6.67 parts by weight of acrylonitrile and a solution of 0.032 part by weight of tert-butyl peroxyisopropyl carbonate in 16.67 parts by weight of toluene were drip-fed through the dropping funnel under reflux at the boiling temperature over a period of two hours. After the completion of this dripfeeding, the solution was continuously stirred for one hour. The polymerization solution consequently obtained was dried under a reduced pressure at 120° C. The produced polymer was converted into a 15% chloroform solution. When this solution was tested for yellow index (YI) by the use of a calorimeter (produced by Nippon Denshoku K.K. and marketed under product code of "Type Σ80") (by the permeation method using the standard plate, No. 1 and a cell of 10 mm), the YI was found to be 2.7.

EXAMPLE 31

A polymerization was carried out by following the procedure of Example 30 while using the acrylonitrile solution of Example 25 obtained after 30 days' storage at 55° C. When the polymer consequently obtained was tested for YI in the same manner as in Example 30, the YI was found to be 5.6.

EXAMPLE 32

A polymerization was carried out by following the procedure of Example 30 while using the acrylonitrile solution of Example 26 obtained after 30 days' storage at 55° C. When the polymer consequently obtained was tested for YI in the same manner as in Example 30, the YI was found to be 4.8.

EXAMPLE 33

A polymerization was carried out by following the procedure of Example 30 while using the acrylonitrile solution of Example 27 obtained after 30 days' storage at 55° C.

When the polymer consequently obtained was tested for YI in the same manner as in Example 30, the YI was found to be 2.7.

EXAMPLE 34

A polymerization was carried out by following the procedure of Example 30 while using the acrylonitrile solution of Example 28 obtained after 30 days' storage at 55° C. When the polymer consequently obtained was tested for YI in the same manner as in Example 30, the YI was found to be 2.7.

Control 7

A polymerization was carried out by following the procedure of Example 30 while using the acrylonitrile solution or Control 6 obtained after 120 days' storage at 70° C. When the polymer consequently obtained was tested for YI in the same manner as in Example 30, the YI was found to be 17.6.

EXAMPLE 35

Crude N-phenyl maleimide (produced by Nippon Shokubai Co., Ltd.) was washed with water, deprived of a solvent, combined with 4-tert-butyl catechol (TBC) (primary antioxidant), and distilled. To the N-phenyl maleimide (containing 0.01% by weight of TBC) distilled in the molten state, tristearyl phosphite (secondary antioxidant) was added in an amount calculated to account for a concentration of 0.1% by weight. The molten solution was treated by a single drum type flake producing device (produced by Kusuki Kikai K.K.) to obtain a solid 1-phenyl maleimide.

In a container made of stainless steel (SUS 304) and having an inner volume of 1 liter, 540 g of the solid N-phenyl maleimide was dissolved in 360 g of acrylonitrile having a water content of 0.41% by weight (produced by Sumitomo Chemical Industry Co., Ltd.) at 40° C. to prepare an acrylonitrile solution of 60% by weight of N-phenyl maleimide.

A nitrogen gas containing molecular oxygen in a concentration of 7% by volume was blown into the solution in the container for thorough displacement of the entrapped air therewith and the gaseous phase part of the container was filled with the same gas. The container was then tightly sealed with a silicone rubber stopper. The solution was then stored at 55° C. for 30 days. The L, a, and b values and the differences thereof before and after the storage were as follows.

Before storage: L=99.5, a=−21.5, b=38.8
After storage: L=99.0, a=−21.2, b=39.3
Difference: $\Delta$L=0.5, $\Delta$a=0.3, $\Delta$b=0.5

Control 8

The procedure of Example 35 was repeated except that the addition of tristearyl phosphite was omitted. The L, a, and b values and the differences thereof before and after the storage were as follows.

Before storage: L=99.5, a=−21.5, b=38.8
After storage: L=98.8, a=−20.9, b=40.6
Difference: $\Delta$L=0.7, $\Delta$a=0.6, $\Delta$b=1.8

Control 9

A solid N-phenyl maleimide was obtained by following the procedure of Example 35 while omitting the addition of tristearyl phosphite. An acrylonitrile solution was prepared by following the procedure of Example 35 while using the solid N-phenyl maleimide instead and also using acrylonitrile having 0.1% by weight (based on the amount of N-phenyl maleimide) of tristearyl phosphite added in advance thereto as acrylonitrile. This acrylonitrile solution was stored at 55° C. for 30 days. The L, a, and b values and the differences thereof before and after the storage were as follows.

Before storage: L=99.5, a=−21.5, b=38.8
After storage: L=99.0, a=−21.0, b=40.4
Difference: $\Delta$L=0.5, $\Delta$a=0.5, $\Delta$b=1.6

EXAMPLE 36

The procedure of Example 35 was repeated except that the N-phenyl maleimide (containing 0.01% by weight of TBC) emanating in a molten state from the distillation column was combined with such an amount of distearyl pentaerythritol diphosphite (secondary antioxidant) as calculated to account for a concentration of 0.1% by weight. The L, a, and b values and the differences thereof before and after the storage were as follows.

Before storage: L=99.5, a=−21.5, b=38.8
After storage: L=99.3, a=−21.2, b=39.4
Difference: a L=0.2, $\Delta$a=0.3, $\Delta$b=0.6

EXAMPLE 37

The procedure of Example 35 was repeated except that the N-phenyl maleimide (containing 0.01% by weight of TBC) emanating in a molten state from the distillation column was combined with triethylene glycol-bis[3-(3-tert-butyl-5-methyl-4-hydroxyphenyl)propionate] and distearyl pentaerythritol diphosphite (both secondary antioxidants) each in an amount calculated to account for a concentration of 0.1% by weight. The L, a, and b values and the differences thereof before and after the storage were as follows.

Before storage: L=99.5, a=−21.5, b=38.8
After storage; L=99.4, a=−21.3, b=39.6
Difference: $\Delta$L=0.1, $\Delta$a=0.2, $\Delta$b=0.8

EXAMPLE 38

The procedure of Example 36 was repeated except that the molten solution of N-phenyl maleimide containing TBC and distearyl pentaerythritol diphosphite was not solidified but was dissolved in its unmodified form in the acrylonitrile solution. The L, a, and b values and the differences thereof before and after the storage were as follows.

Before storage: L=99.5, a=−21.5, b=38.8
After storage: L=99.4, a=−21.4, b=39.1
Difference: $\Delta$L=0.1, $\Delta$a=0.1, $\Delta$b=0.3

EXAMPLE 39

An acrylonitrile solution was obtained by following the procedure of Example 35 while adding distearyl pentaerythritol diphosphite (secondary antioxidant) in an amount calculated to account for a concentration of 0.1% by weight to the N-phenyl maleimide (containing 0.01% by weight of TBC) emanating from the distillation column thereby obtaining a N-phenyl maleimide in a solid state, and then allowing the solid N-phenyl maleimide to stand for 3 months. The L, a, and b values and the differences thereof before and after the storage were as follows.

Before storage: L=99.5, a =−21.5, b=38.8
After storage: L=99.3, a=−21.2, b=39.5
Difference. $\Delta$L=0.2, $\Delta$a=0.3, $\Delta$b=0.7

Control 10

The procedure of Example 39 was repeated except that the addition of distearyl pentaerythritol diphosphite was omitted. The L, a, and b values and the differences thereof before and after the storage were as follows.

Before storage: L=99.5, a=−21.5, b=38.8
After storage: L=98.3, a=−20.1, b=41.5
Difference: ΔL=1.2, Δa=1.4, Δb=2.7

What is claimed is:

1. A method for the storage of an acrylonitrile solution of N-phenyl maleimide, which, in a forced coloration test, the values, ΔL, Δa, Δb, are calculated in accordance with the following formulas:

$$\Delta L=|L1-L2|\text{(Absolute value)}$$

$$\Delta a=|a1-a2|\text{(Absolute value)}$$

$$\Delta b=|b1-b2|\text{(Absolute value)}$$

wherein L1, a1, and b1 are respectively the values of L, a, and b of said acrylonitrile solution before undergoing said forced coloration test and L2, a2, and b2, are respectively the values of L, a, and b of said acrylonitrile solution after undergoing said forced coloration test and are respectively 5 or less, 5 or less and 10 or less, wherein a molecular oxygen concentration of the gaseous phase portion of said solution is adjusted to a level in the range of 0.01 to 10% by volume preparatorily to storing said solution in contact with a metal, and water content is not more than 0.1% by weight.

2. The method according to claim 1, wherein the acrylonitrile solution comprises from 0.0001 to 1% of at least one primary antioxidant selected from the group consisting of alkyl-substituted hydroxybenzenes and hindered phenols relative to the maleimide and, from 0.0001 to 1% of at least one secondary antioxidant selected from the group consisting of phosphorous esters, phosphoric esters, phosphine, and phosphoric acid amides relative to the maleimide.

3. The method according to claim 2, which comprises the steps of:

preparing the maleimide mixture by adding the primary antioxidant and the secondary antioxidant to the maleimide in a molten state and, subsequently dissolving said maleimide containing mixture in acrylonitrile.

4. The method according to claim 2, comprising:

adding a primary antioxidant and a secondary antioxidant to acrylonitrile and, dissolving molten maleimide therein.

5. The method according to claim 1, wherein the concentration of N-phenyl maleimide in acrylonitrile is between 40 to 90% by weight relative to that of the acrylonitrile solution of N-phenyl maleimide.

6. The method according to claim 1, wherein said gaseous portion comprises molecular oxygen and an inert gas selected from the group consisting of nitrogen, carbon dioxide, helium and argon.

7. The method according to claim 6, wherein said inert gas is nitrogen.

8. A method for the storage of an acrylonitrile solution of N-phenyl maleimide, which, in a forced coloration test, the values, ΔL, Δa, Δb, are calculated in accordance with the following formulas:

$$\Delta L=|L1-L2|\text{(Absolute value)}$$

$$\Delta a=|a1-a2|\text{(Absolute value)}$$

$$\Delta b=|b1-b2|\text{(Absolute value)}$$

wherein L1, a1, and b1 are respectively the values of L, a and b of said acrylonitrile solution before undergoing said forced coloration test and L2, a2, and b2, are respectively the values of L, a, and b of said acrylonitrile solution after undergoing said forced coloration test and are respectively 5 or less, 5 or less and 10 or less, wherein a molecular oxygen concentration of the gaseous phase portion of said solution is adjusted to a level in the range of 0.01 to 10% by volume preparatorily to storing said solution in contact with a metal, wherein the acrylonitrile solution has a water content of not more than 0.3% by weight in the presence of at least one member selected from alkyl-substituted hydroxybenzenes, hindered phenols, phosphorous esters, phosphoric esters, and phosphoric acid amides.

9. The method according to claim 8, wherein a total amount of azobenzene and N,N-diphenyl hydrazine is not more than 500 ppm.

10. The method according to claim 8, wherein the concentration of N-phenyl maleimide in acrylonitrile is between 40 to 90% by weight relative that of the acrylonitrile solution of N-phenyl maleimide.

* * * * *